(12) United States Patent
Johnson et al.

(10) Patent No.: US 6,330,343 B1
(45) Date of Patent: Dec. 11, 2001

(54) METHOD FOR MEASURING COKE QUALITY BY DIGITAL QUANTIFICATION OF HIGH INTENSITY REFLECTIVITY

(75) Inventors: Paige Lea Johnson, Owasso; Hooshang Jozavi, Ponca City, both of OK (US)

(73) Assignee: Conoco Inc., Houston, TX (US)

( * ) Notice: Subject to any disclaimer, the term of this patent is extended or adjusted under 35 U.S.C. 154(b) by 0 days.

(21) Appl. No.: 09/258,859

(22) Filed: Feb. 26, 1999

(51) Int. Cl.[7] ........................................ G06K 9/00
(52) U.S. Cl. .................................................. 382/100
(58) Field of Search ................................. 382/100, 141, 382/286, 312, 321; 348/86, 92, 125, 127, 128, 130, 131, 180; 356/300, 388, 432, 445, 448, 213, 216, 237.1, 240.1, 237.2, 911, 927, 928; 702/1, 22, 81, 82, 83, 84, 127, 130, 136, 155, 156, 189, 190, 198

(56) References Cited

U.S. PATENT DOCUMENTS

| | | | |
|---|---|---|---|
| 4,617,682 | * | 10/1986 | Mori et al. ............................ 382/108 |
| 5,132,791 | * | 7/1992 | Wertz et al. ........................... 348/88 |
| 5,432,595 | * | 7/1995 | Pechersky ............................ 356/35.5 |
| 5,440,648 | * | 8/1995 | Roberts et al. ....................... 382/141 |
| 5,443,164 | * | 8/1995 | Walsh et al. .......................... 209/580 |
| 5,828,500 | * | 10/1998 | Kida et al. ............................ 359/798 |

OTHER PUBLICATIONS

"Evaluation of Needle Coke Appearance By Illumination By Reflected Light", Koa Poster at 1997 Carbon Conference, K. Matsuoaka, T. Fujii, Y. Fujii, T. Miura, T. Oyama and E. Kitajima, Needle Coke Quality Control and Research Laboratory Section, Marifu Refinery, Koa Oil Co., Ltd.

Koa Pre–Prints to 1997 Carbon Conference; "Carbon '97", 23rd Biennial Conference on Carbon Jul. 18–23, 1997; Extended Abstracts and Program, vol. II—Carbonization/Industrial/Carbon Growth/Fibers., The American Carbon Society and PennState, "Evaluation of Needle Coke Appearance by Illumination by Reflected Light", pp. 238–239.

"Digital Image Analysis: Basic Principles and Industrial Research Applications", by Paige Johnson of Conoco, Inc., Presented at the OSU College of Osteopathic Medicine, Feb. 26, 1998.

* cited by examiner

*Primary Examiner*—Andrew W. Johns
*Assistant Examiner*—Shervin Nakhjavan
(74) *Attorney, Agent, or Firm*—Head, Johnson & Kachigian

(57) ABSTRACT

The invention includes an improved test for quantifying lustre of petroleum products in particle form, especially coke, as an index of quality. The test involves obtaining and preparing a sample and then placing it beneath an illuminating device in a manner that promotes the formation of a substantially smooth upper surface. The illuminating device uses visible light from a desired direction to produce a visible light pattern from the light reflected from the sample's upper surface. The pattern is then acquired to capture an image. The sample may be slightly magnified for acquisition of the image. The pattern may be acquired multiple times to develop an average image. The image is then processed digitally to produce a representative lustre measurement for the sample. The preceding process may be repeated several times for each sample and the resultant lustre measurements for each iteration are totalled and averaged. Once the lustre measurement for the sample is obtained, it is compared to established parameters to assign a CTE value to the sample, assuming there is sufficient historical data correlating the two measurements. Various refining operating parameters including feedstocks, temperatures and pressures, may be altered to obtain a desired product.

20 Claims, 14 Drawing Sheets

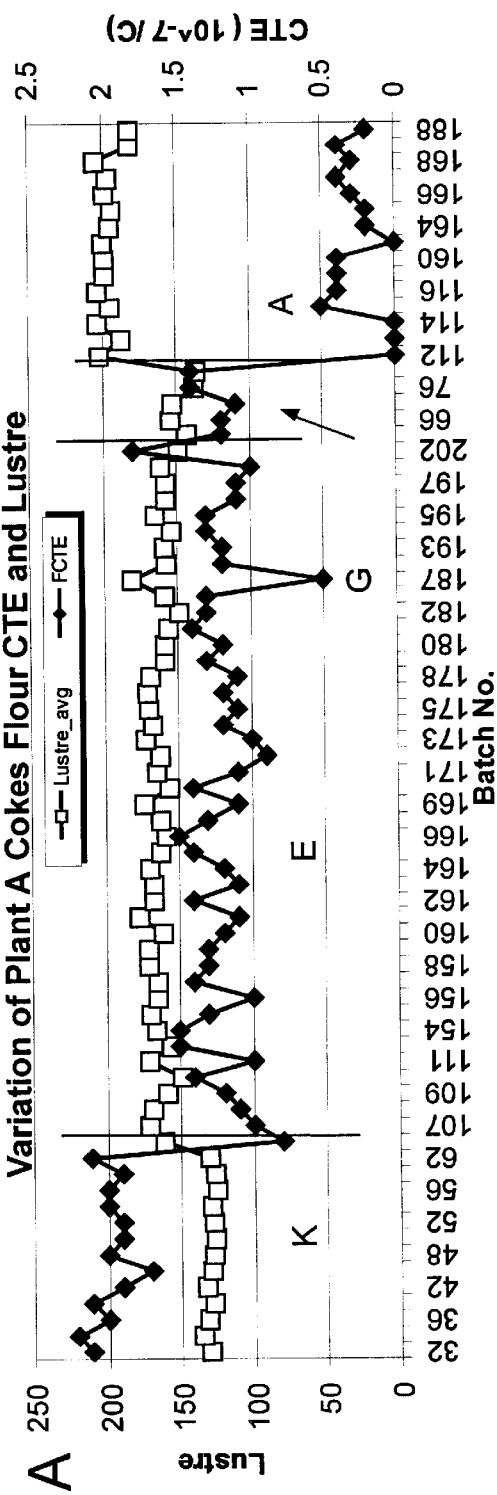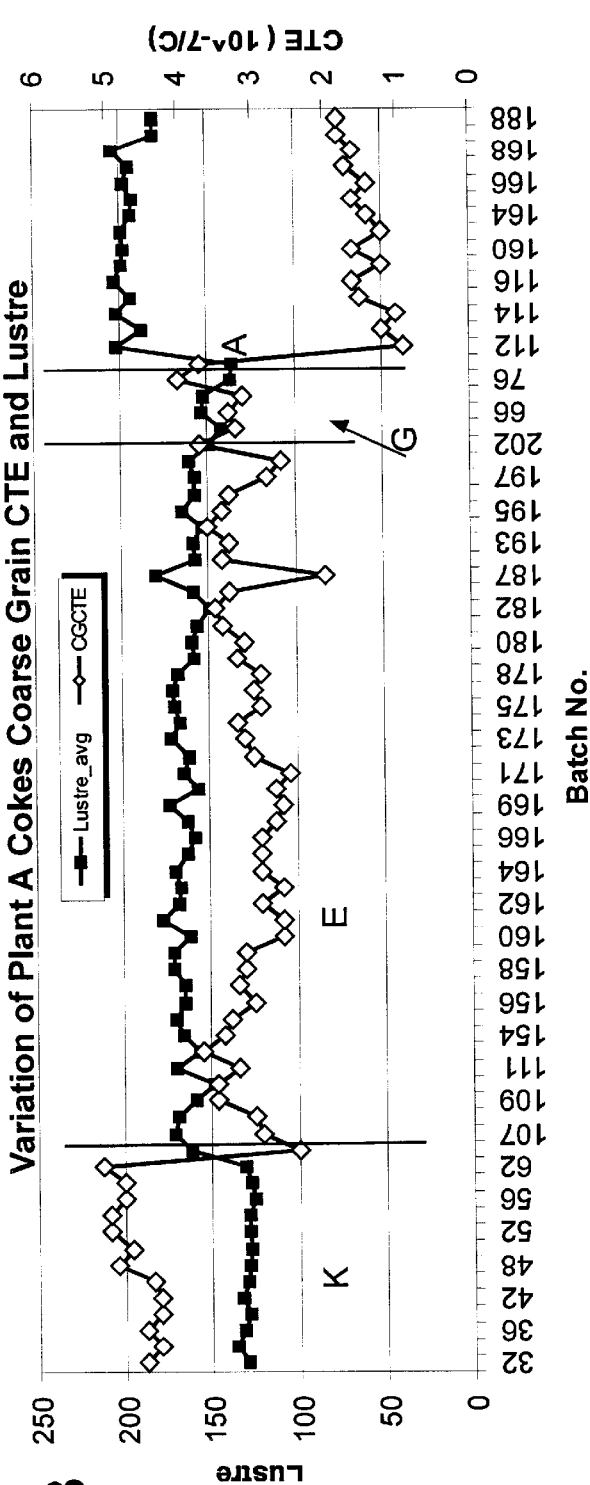
FIG. 1A
FIG. 1B

FIG. 6 Comparison of Calcined Cokes Based on Measured and Lustre-predicted Coarse Grain CTEs (see Table 2)

Monitor 980029
Lustre Average
(see Table B2)

UCL = 186.66
Centerline = 179.83
LCL = 173.01
n= 5, Sig (x) = 5.1; Sig(x-bar) =2.3

Monitor 980029
Coke Lustre Range Chart
( see Table B2)

UCL = 25.02
Centerline = 11.83
LCL = 0.00

METHOD FOR MEASURING COKE QUALITY BY DIGITAL QUANTIFICATION OF HIGH INTENSITY REFLECTIVITY

BACKGROUND OF THE INVENTION

1. Field of the Invention

The present invention relates generally to an improved method of analyzing petroleum products in particle form. More particularly, the present invention relates to an improved method for analyzing the quality of petroleum by-products in particle form, especially coke, and relates to improved methods for refining petroleum to obtain desirable coke by-products.

2. Prior Art

As will be appreciated by those skilled in the art, petroleum products are analyzed for many purposes by using various tests. The test results are used for many purposes, sometimes even including controlling the refining of these products in order to achieve desired results but more often for appropriately classifying the products for subsequent sale.

For example, coke is a resulting by-product from petroleum refining that must be appropriately classified prior to sale. Cokes are typically classified by measuring their coefficient of thermal expansion (CTE) which provides the rate of expansion (or contraction) of a substance with temperature change.

In one use, coke is used in manufacture of large graphite electrodes for electric arc furnaces employed in the steel industry. It is known that cokes with lower CTE (e.g. FCTE=0.0–2.0×10$^{-7}$/° C.) result in better performance of graphite electrodes under electric arc furnace (EAF) operations than those with higher CTE (e.g. FCTE>4.0×10$^{-7}$ C.). Therefore, lower CTE cokes are more desirable than higher CTE cokes.

It is believed that, in typical representative coke samples, the lower CTE materials consist of a larger number (percent) of highly needle-like particles than the higher CTE materials. Needle-like particles are those whose structure has a preferential orientation. They are generally elongated as a result; hence the term "needle". For a particular premium coke grade, the needle-like structure is not constant throughout the coke particles of that grade. Instead, there is a distribution of highly needle-like to highly non-needle-like particles.

One known method of classifying coke involves testing or examining these calcined cokes to determine the coke CTE. This procedure involves extrusion of a mixture of calcined coke particles and a binder pitch followed by baking, graphitizing and measurement of CTE of the resulting artifacts. Typically, the artifact is heated and measurements are taken at various temperatures to determine the CTE for a particular batch of coke. As will be appreciated by those skilled in the art, this procedure is fairly involved and time-consuming, on the magnitude of three to four days for a CTE measurement.

The resulting CTE determination has been previously used to segregate cokes into quality grades. However, the known methods for measuring coke CTE are complex and time-consuming. Thus, an improved method for classifying cokes is desirable.

It has been observed that, to even an untrained eye, higher quality cokes are shinier than lower quality ones. Subsequent research has shown (KOA Oil Company, 1997 Carbon Conference, PSU) that there is a correlation between CTE measurements and the "shininess" of a field of coke particles.

Another method of classifying coke is to use the varying reflectivities of the coke. The lustre method of the present invention quantifies this visual perception by digitally measuring the reflection of light from a pan of coke particles. This measurement is the coke's lustre (hereinafter, the phrase "coke lustre" will be used to refer to the intensity of visible light reflected from the surface of a coke particle or a layer of coke particles). The measurement of coke lustre is approximately analogous to extracting and counting the particles with the most needle-like character. Thus, coke lustre reveals information that can be used for ranking cokes based on their needle-like structure that is similar to CTE measuring methods.

Measuring coke lustre is easier than other known methods of physically measuring coke CTE. Classification of cokes based on lustre measurements has been difficult because only small differences in lustre are seen, even when CTE differences are significant. In other words, it has been difficult to correlate the small deviations noticed between coke lustres with a meaningful correlation with CTE variances.

Therefore, a need exists in the art for an improved method of classifying coke. A particularly desirable improvement would be an improved method of classifying coke based on its reflectivity or lustre as opposed to existing methods of physically measuring coke CTE. An even more desirable improvement would be a method for increasing the accuracy and reliability of such a lustre classification method.

SUMMARY OF THE INVENTION

The present invention addresses the above referenced needs in the art. In an exemplary embodiment, the invention provides a method for measuring coke quality by digital quantification of high intensity reflectivity. The invention includes an improved test for qualifying petroleum products, especially coke. The test involves obtaining a sample from a petroleum product (i.e. calcined coke) produced under known operating parameters during petroleum refining. The test enables the user to quickly and efficiently classify the product.

The test generally includes several broad steps. The first step is to obtain a representative sample for the target product, in the exemplary process coke, although the test may work well for other types of petroleum products as well.

The representative sample is then prepared in accordance with standard laboratory protocols (i.e. sieving, de-oiling, etc.) until the sample is properly suited for further testing. The properly prepared sample is then appropriately placed beneath an illuminating device in a manner that promotes the formation of a substantially smooth upper surface. This may require physical leveling of the sample or the like. The critical consideration is that the upper surface of samples being tested are prepared in an uniform manner to remove or at least curtail errant deviations from the test procedure.

The sample is then exposed to illumination. Preferably, a ring light or other lighting mechanism is deployed to shine on the sample with visible light from a desired direction (i.e. directly over the top surface of the sample). The illumination produces a visible light pattern from the light reflected from the sample's upper surface. As discussed previously, the reflectivity or lustre of a particular sample due to the illumination varies in correlation to the sample's CTE.

The pattern resulting from the illumination is then acquired to capture a digital image of the reflection of the sample. In a preferred embodiment, the digital image was acquired through use of a photography camera. In some circumstances, it may be desirable to slightly magnify the sample for acquisition, but this is not always necessary. Of course, the magnification can be accomplished with lenses or in other conventional manners.

Preferably, the pattern is acquired multiple times to develop an average image to reduce noise. In practice, the pattern was acquired 16 times consecutively although the multitude of acquisitions can be increased or diminished as desired.

Once a representative image has been obtained, it is processed digitally. The digital image is then quantified by measuring the gray levels present in the image. The highest gray levels are extracted and measured to produce a representative lustre measurement for the sample. During this extraction and measurement, a computer is preferably used to select the highest gray levels although specialized equipment having pattern recognition digital processing functions capable of producing and defining the video image as having a low or high CTE may be alternatively employed.

Ideally, the preceding process is repeated several times for each sample and the resultant lustre measurements for each iteration are totalled and averaged to avoid potential errors or deviations. In this manner, a more accurate representative lustre measurement is obtained.

Once the lustre measurement for the sample is obtained, it can be easily related to the CTE of the sample given sufficient historical correlation between the types of measurements.

In order to obtain a desired product (coke with a desired CTE), the various operating parameters of the refining process may be varied until the desired product is obtained. Changes to the operating parameters necessarily alter the lustre (and CTE of the coke), which can then be subsequently remeasured and compared to a desired value. The user may continue to alter the operating parameters until a desirable coke product is obtained as indicated by the resulting lustre or CTE value.

Thus, a principal object of the present invention is to provide an improved method of testing petroleum products for classification.

A basic object of the present invention is to provide a method for varying operating parameters in a petroleum refining process to produce a desirable product.

A related object of the present invention is to increase the efficiency of petroleum processing by providing an improved test that enables users to more quickly classify products.

Another object of the present invention is to provide an improved test that enables users to accurately classify coke products using lustre.

Another object of the present invention is to provide an improved test that increases the reliability of petroleum product classification.

A basic object of the present invention is to provide more efficient refining of petroleum products Another basic object of the present invention is to provide an improved test that reliably measures coke lustre which is closely related to coke coefficient of thermal expansion (CTE).

BRIEF DESCRIPTION OF THE DRAWINGS

FIG. 1a is a graph depicting variation of Plant A of cokes flour CTE and lustre;

FIG. 1b is a graph depicting variation of Plant A of cokes coarse grain CTE and Lustre;

DETAILED DESCRIPTION OF THE PREFERRED EMBODIMENTS

Figure 7:
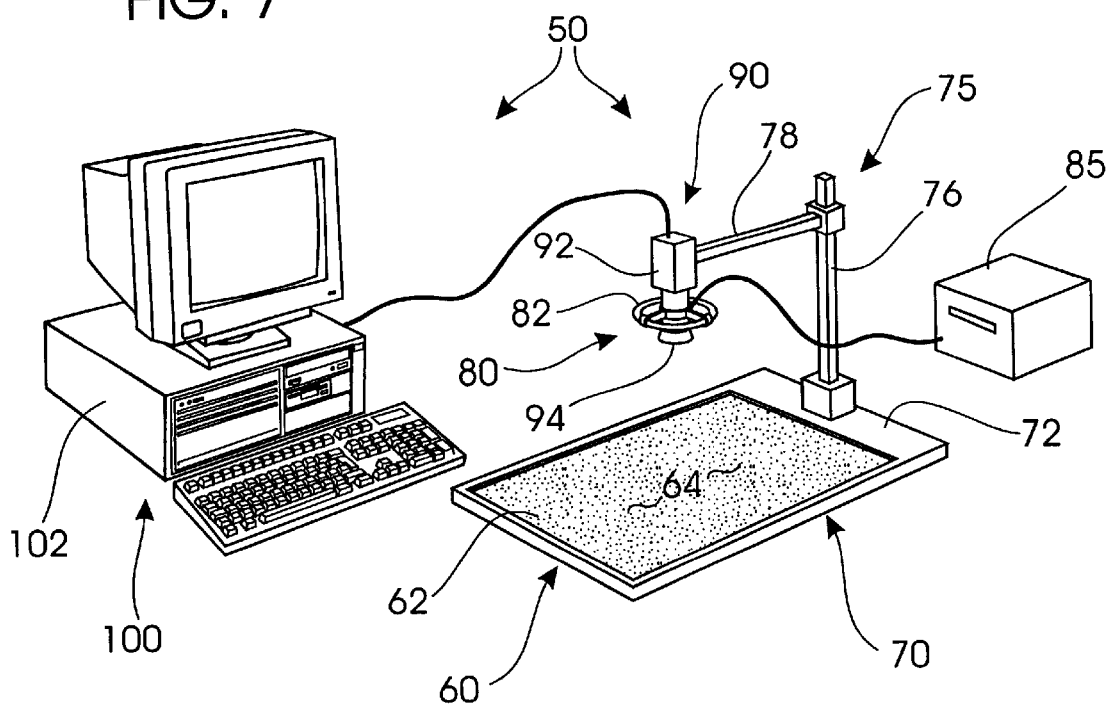
FIG. 7 is a schematic representation of an exemplary embodiment in accordance with the present invention.
Figure 8:
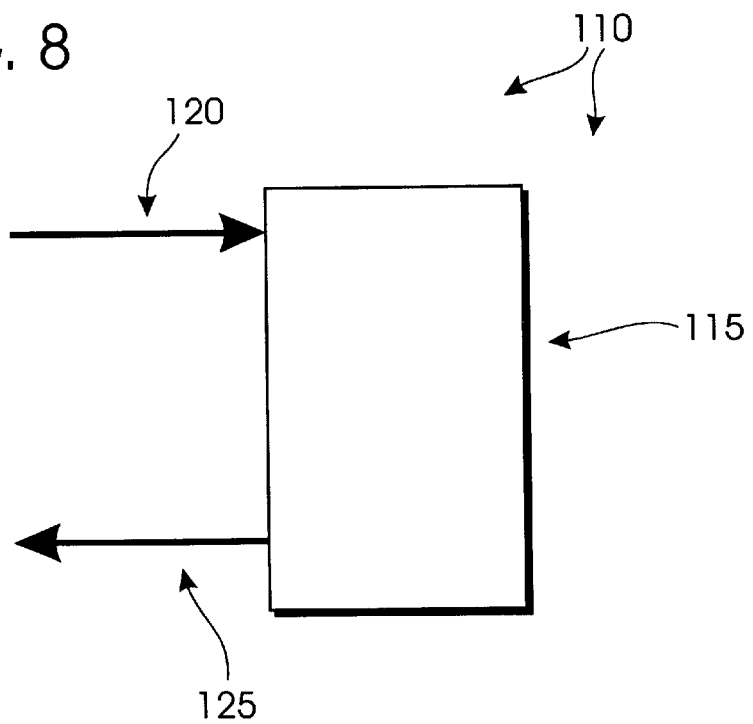
FIG. 8 is a block diagram of the coking portion of a petroleum refining process in accordance with the present invention.

The present invention provides a method for measuring quality of petroleum products in particle form by digital quantification of high intensity reflectivity. Referring initially to FIGS. 7 and 8, in an exemplary embodiment, the invention includes an improved test using system 50 (FIG. 7) for determination of quality of petroleum cokes. Heretofore, cokes have typically been classified by quantifying coefficient of thermal expansion (CTE). The test involves obtaining a sample 60 from a petroleum product (i.e. coke) produced under known operating parameters during petroleum refining 110 (FIG. 8). The test 50 enables the user to quickly and efficiently classify the product.

The test generally includes several broad steps. The first step is to obtain a representative sample 60 for the target product, generally coke, although the test may work well for other types of petroleum products as well.

The representative sample 60 is then prepared in accordance with standard laboratory protocols (i.e. sieving, de-oiling, etc.) until the sample 60 is properly suited for further testing. The properly prepared sample 62 is then appropriately placed in a tray 70 or similar container.

The tray 70 facilitates the formation of a smooth upper surface 64 in sample 62. The surface 64 may require additional physical leveling of the sample 62 or the like to attain a sufficiently flat surface. The critical consideration is that the upper surface 64 of various samples be prepared in an uniform manner to remove or at least curtail errant deviations from the test 50. The tray 70 may also include a stand 75 selectively offset from the tray floor 72 by a support rod 76. The rod 76 protrudes upwardly from the floor 72 and supports an elongated holder 78. The holder 78 may mount a lighting device 80 and an analog or digital imager 90, but need not necessarily do so.

In a preferred embodiment, the tray 70 and sample 60 are disposed beneath a lighting device 80 and a digital camera 90. The lighting device 80 may comprise a ring light 82 or similar device controlled by power supply 85. Ideally, power supply 85 ensures an invariant power source for the lighting device 80 to prevent deviations in test apparatus 50. The tray 70 and particularly surface 64 are ideally centered directly beneath light 82 and imager 90.

Once properly positioned, the sample 62 is then exposed to illumination by activating the light 82. Preferably, the ring light 82 or other lighting mechanism is deployed to shine on the sample 62 and more particularly the surface 64 with visible light from a desired direction (i.e. directly over the top surface of the sample). This illumination produces a visible light pattern from the light either reflected or emitted from the sample's upper surface 64. As discussed previously, the reflectivity or lustre of a particular sample due to the illumination has been found to be in correlation to the sample's CTE.

The pattern resulting from the illumination is then acquired by the imager 90. Imager 90 may be an analog or digital camera 92 or other similar, conventional device that can capture an image of the reflection of the sample. Preferably, the pattern is acquired multiple times to develop an average image to reduce potential errors.

In some circumstances, it may be desirable to slightly magnify (in the order of 05.x to 10x) the sample, but this is not always necessary. Magnification can be accomplished with lens 94 or in any other conventional manner.

Once a representative image has been obtained, it is transmitted to an associated digital processor 100. The processor may include image analysis software and a frame grabber board which converts an analog signal to a digital signal. If a digital camera is used, a frame-grabber is not necessary because the signal is already digital. A bit map of the image is produced which has X and Y coordinates and a gray level for each point, or pixel, in the image. The digital video image is then quantified by measuring the gray levels present in the image. The gray levels are measured from 0 being the blackest to 255 being the whitest The data is stored as a set of numbers. The highest gray levels are extracted by measured produce a representative lustre measurement for the sample. In the present case, the gray levels over a certain threshold number are selected and extracted. During this extraction and filtration, a personal computer 102 having a central processing unit is preferably used to select the highest gray levels although specialized equipment having pattern recognition digital processing functions capable of producing and defining the video image as having a low or high lustre may be alternatively employed.

Ideally, the preceding process is repeated several times for each sample and the resultant lustre measurements for each iteration are totalled and averaged to avoid potential errors or deviations In this manner, a more accurate representative lustre measurement is obtained. Once the lustre measurement for the sample is obtained, it can be easily related to the CTE of the sample given sufficient historical correlation between the two measurements.

The process for production of coke broadly involves the thermal decomposition of heavy liquid hydrocarbons to produce gas, liquid and coke. Those salable products are produced by fractionation and separation by boiling ranges in the refining process. In order to obtain a desired product (coke) with a desired CTE, it becomes a matter of varying the various operating parameters (represented by box 115) of the refining process 110 until the desired product (represented by output line 125) is obtained (FIG. 8). Changes to the operating parameters can include changing feedstocks, changing operational temperatures, changing operational pressures and the like (represented by input line 120). These changes necessarily alter the coke composition and affect the lustre (and CTE of the coke), which can then be subsequently remeasured and compared to a desired value. The operating parameters continue being altered until a desirable coke product is obtained as indicated by the resulting lustre value.

The coke lustre measurements of the present invention can also help in blending various grades of coke with different quality as determined by their CTEs to result in a blended coke with desirable lustre or desirable CTE properties. For example, if various quality cokes have different lustre, a mixture may be blended to obtain a blended coke with a desirable level of net composite lustre.

EXAMPLE 1

Lustre testing as described hereinabove was performed in accordance with an exemplary embodiment of the invention (FIGS. 7–8). The lustre test results are the average of five separate measurements on the same coke sample. As described hereinafter, for the lustre test measurements, about 400–500 grams of de-oiled and crushed (28/100 ty—Tyler standard screen scale fractions are used). The lustre tests performed on the 131 cokes under study (see Table B1) were done in batches of 10 per day over approximately a two-month period. A monitor coke test was done prior to and followed by the measurements of the 10 daily coke samples. Therefore, the stability of the test was checked and controlled over time.

Figure 2A:
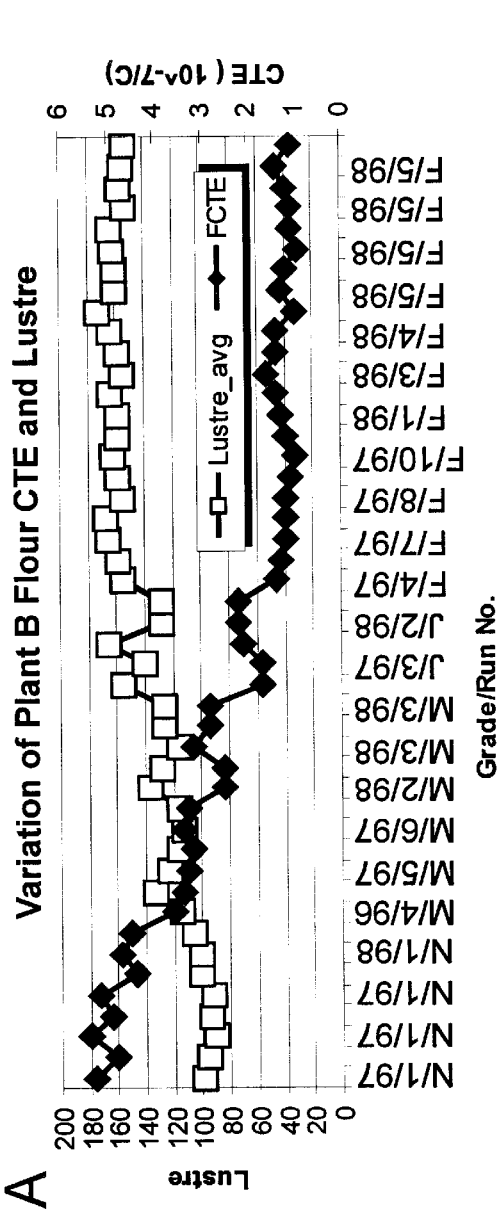
FIG. 2a is a graph depicting variation of Plant B of flour CTE and Lustre.
Figure 2B:
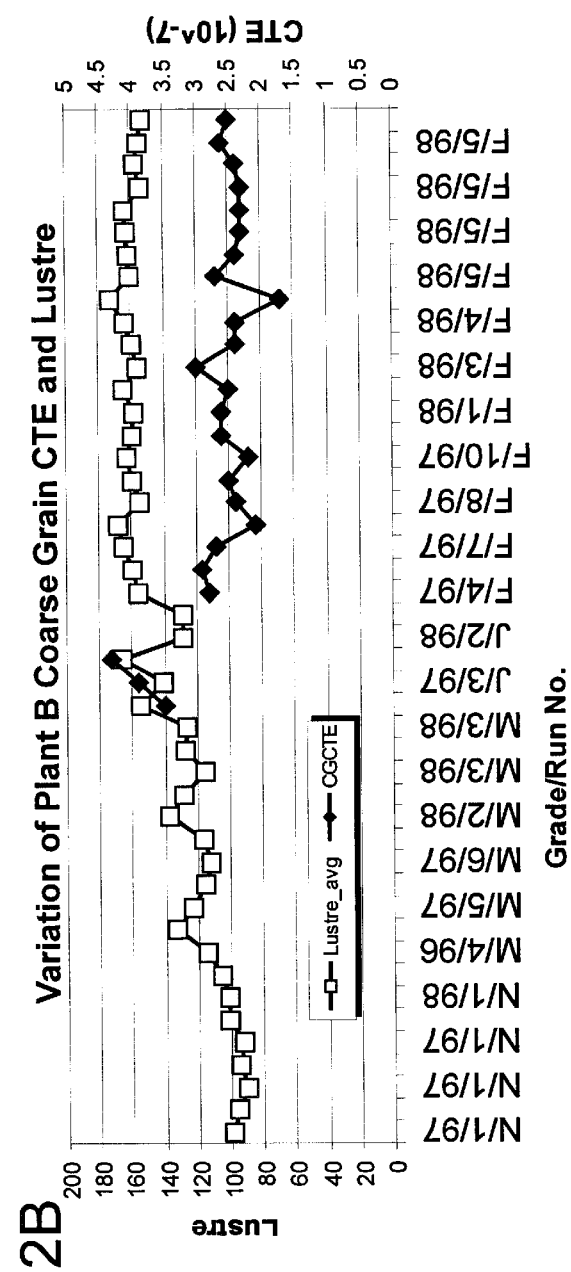
FIG. 2b is a graph depicting variation of Plant B of coarse grain CTE and Lustre.
Figure 3A:
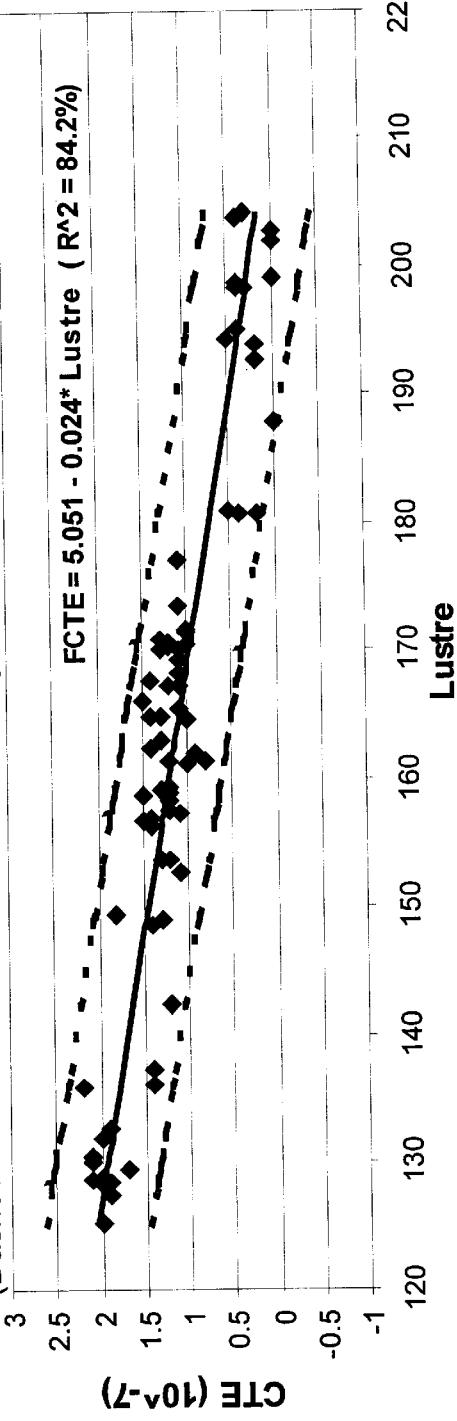
FIG. 3a is a graph depicting relation between samples of Plant A cokes CTE and Lustre.
Figure 3B:
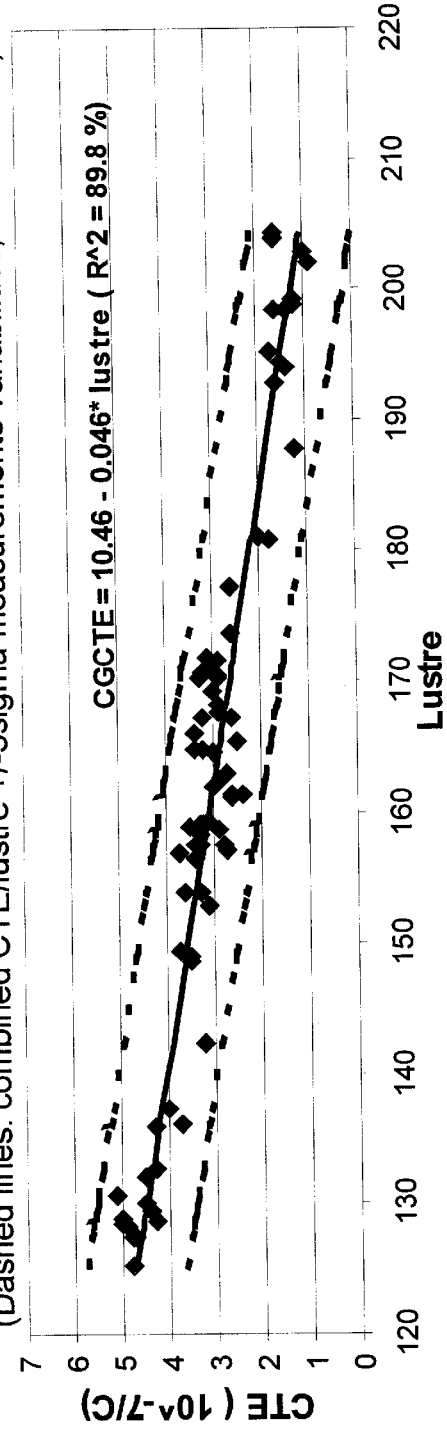
FIG. 3b is a graph depicting relation between Plant A cokes coarse grain CTE and Lustre.
Figure 4:
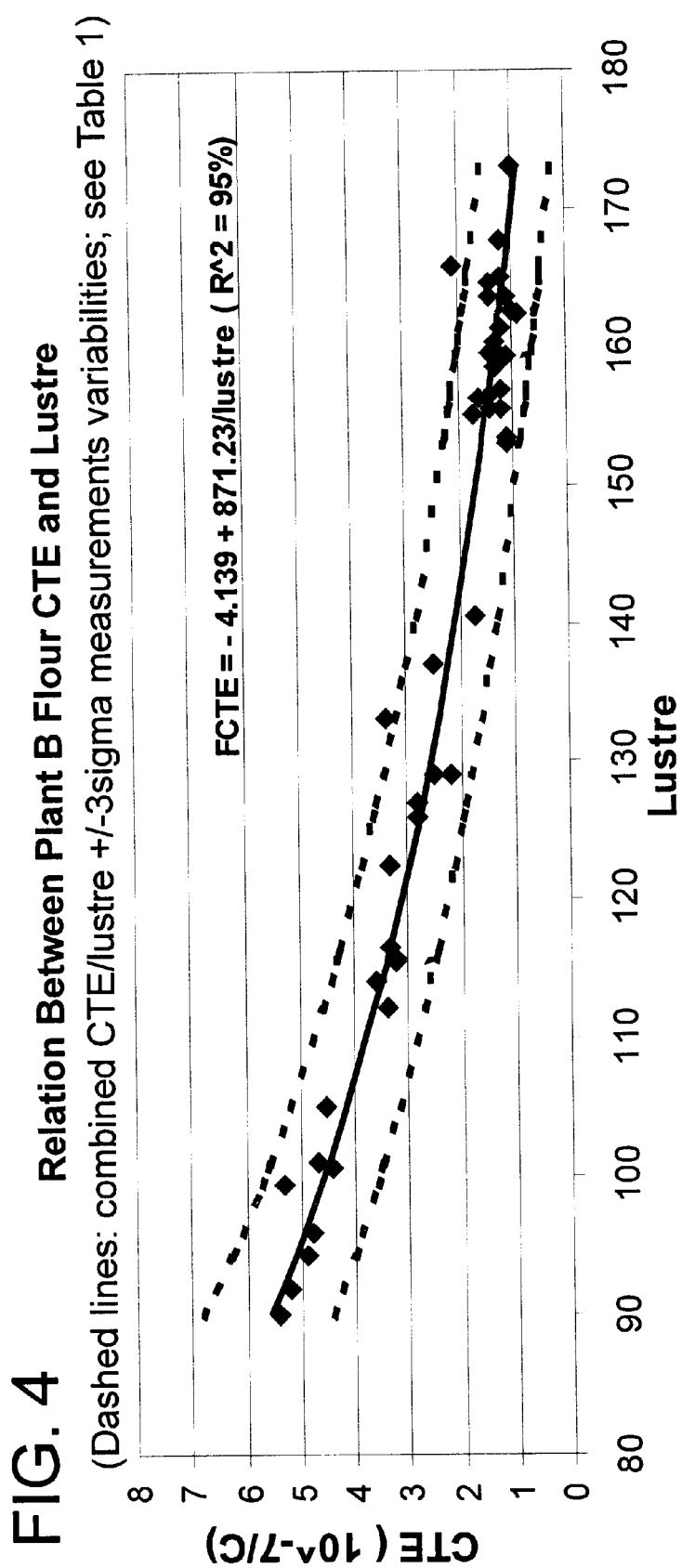
FIG. 4 is a graph depicting relation between Plant B cokes flour CTE and Lustre.

FIGS. 1 and 2 show the comparative ranking of production cokes produced over time based on CTEs and lustre measurements. It is clear that the lustre data closely track the cokes CTEs. The simple regressions (maximum $R^2$ criteria) shown in FIGS. 3 and 4 indicate excellent relations between plant generated CTEs and lustre given the combined lustre/CTE measurement variabilities. The dashed lines in FIGS. 3 and 4 were obtained by translation of the mean regression lines in the horizontal and vertical directions by the ±3σ values (see Table 1) of the corresponding measurements.

Figure 5:
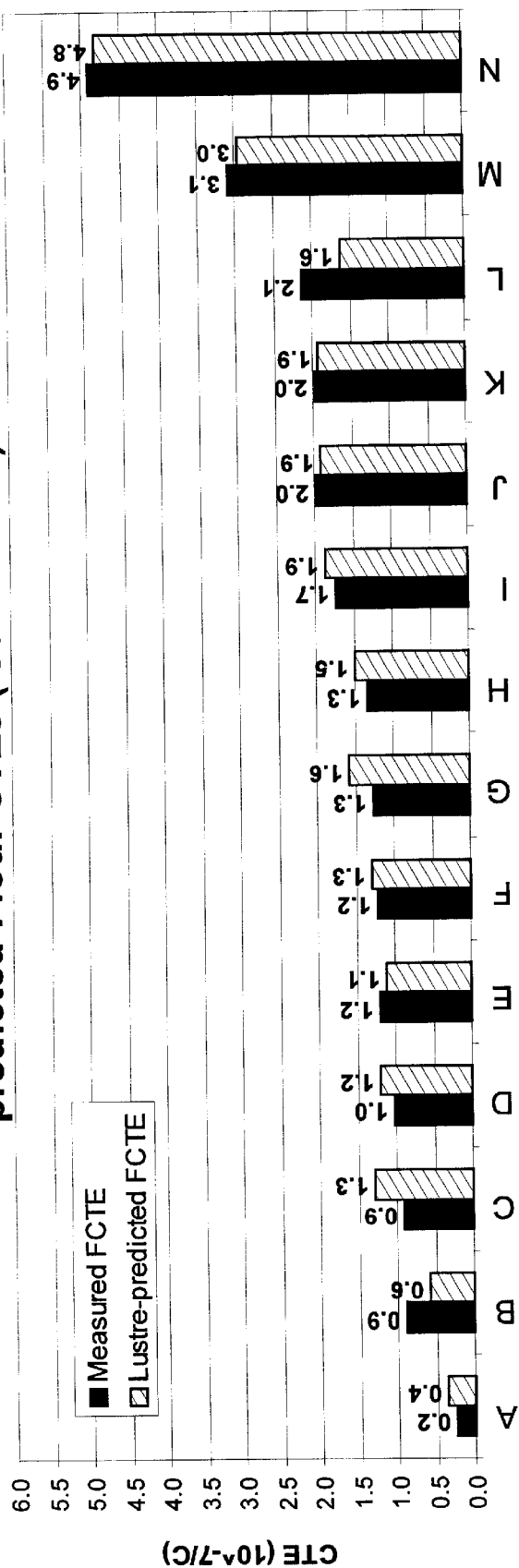
FIG. 5 is a graph depicting comparison of calcined cokes based on measured and lustre-predicted Flour CTEs.
Figure 6:
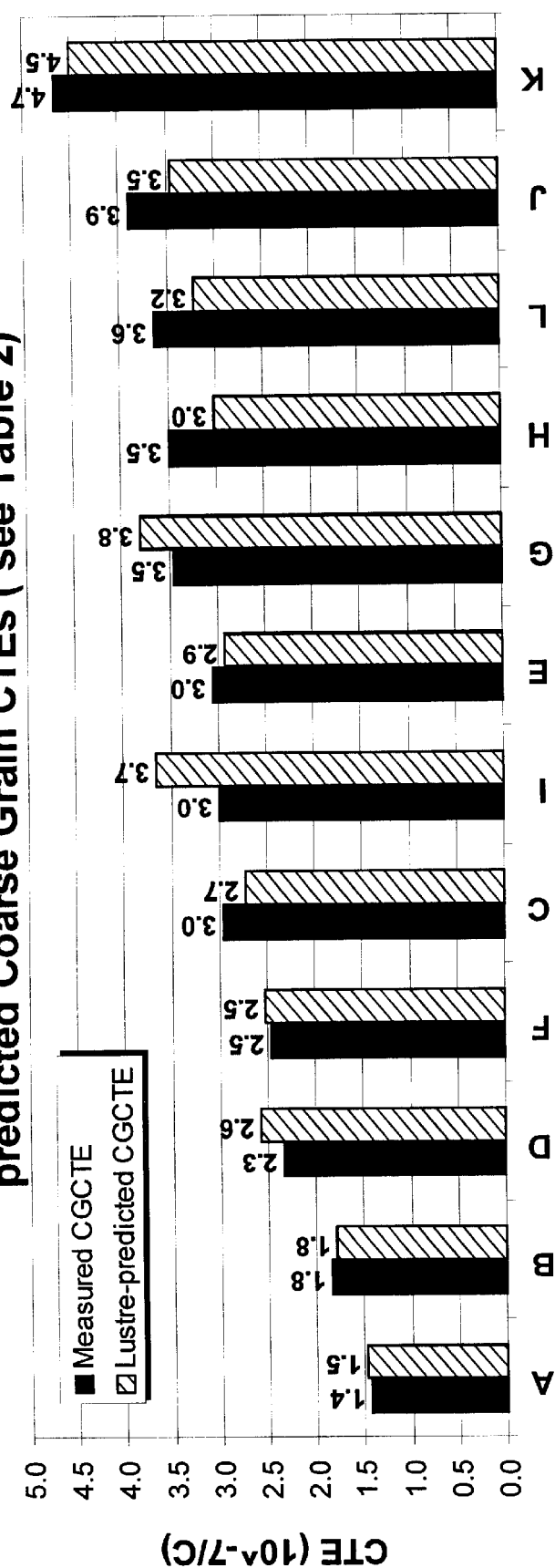
FIG. 6 is a graph depicting comparison of calcined cokes based on measured and lustre-predicted Coarse Grain CTEs.

The average CTEs and lustre properties of the cokes under study along with lustre-predicted average CTEs (by coke grade and source) are shown in Table 2 and FIGS. 5 and 6. Referring to Table 2, there appears to be excellent correlation and agreement between actual CTEs and the lustre-predicted CTEs.

Based on the above findings regarding the low variability of the lustre test as well as its excellent correlation with CTEs, it is believed that significant advantages will be achieved since the lustre test is relatively simple and fast. Therefore, it is cheaper to maintain and easier to control as compared with conventional CTE measurement processes based on baked and extruded artifacts.

The following procedures were employed in the foregoing example:

Sample Preparation

Time required for one sample: 1.7 hours
1. Riffle sample to obtain a representative portion (~1000 g)
2. Sieve to remove natural 28/100 particles
3. De-oil (stays in oven ~24 hours)
4. Crush and sieve coke to obtain ~400 g of 28/100 Ty particles

Sample Analysis

Time required for one sample: 10 minutes
1. At beginning and end of each day, analyze the coke reference sample for SPC purposes.
2. Pour coke into sample tray and smooth surface.
3. Place sample tray under camera, activate program.
4. Computer automatically takes the average of 16 frames acquired consecutively.
5. Re-Pour and analyze sample five times.

The present invention may be applied and utilized in the petroleum refining process as a quality evaluation for coke as a part of the refining process, including but not limited to identifying the effect of product or feedstock changes on the suitability of petroleum coke for particular applications.

Additionally, while the foregoing has been specifically described with relation to coke, the teachings of the invention may be equally pertinent to other petroleum products in particle form.

Whereas, the present invention has been described in relation to the drawings attached hereto, it should be understood that other and further modifications, apart from those shown or suggested herein, may be made within the spirit and scope of this invention.

TABLE 1

Comparison of CTEs and Lustre Measurements Variabilities

| | Test | | | | | |
| --- | --- | --- | --- | --- | --- | --- |
| | Flour CTE Monitor (950169) | | Coarse Grain CTE Monitor (950169) | | Lustre Monitor (980029) | |
| Lab | Mean | 3σ | Mean | 3σ | Mean | 3σ |
| Plant B | 1.60 | 0.45 | 4.11 | 0.55 | — | — |
| Plant A | 1.80 | 0.42 | 4.13 | 0.73 | — | — |
| Plant C | 2.12 | 0.55 | 4.38 | 0.32 | 180 | 6.9 |

Figure 9:
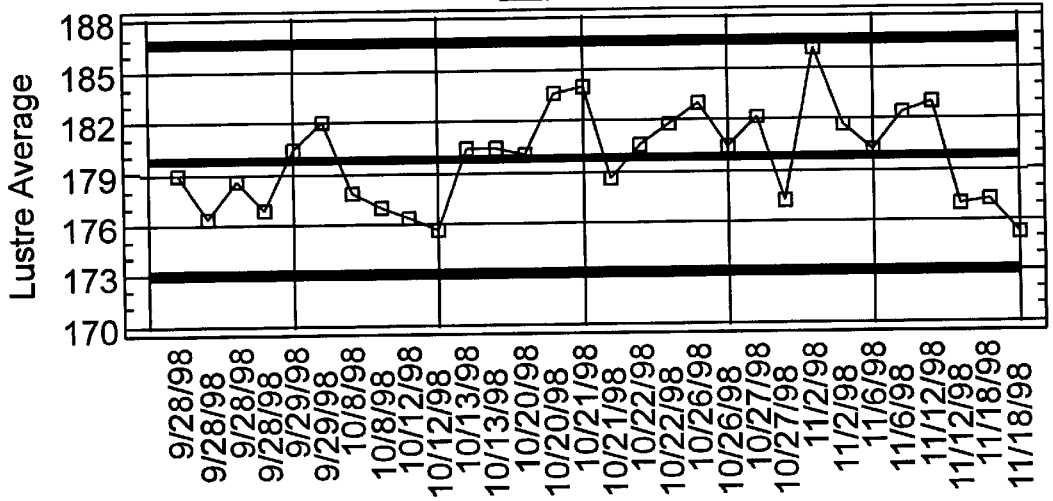
FIG. 9 is a graph depicting coke lustre average for Monitor 980029.
Figure 10:
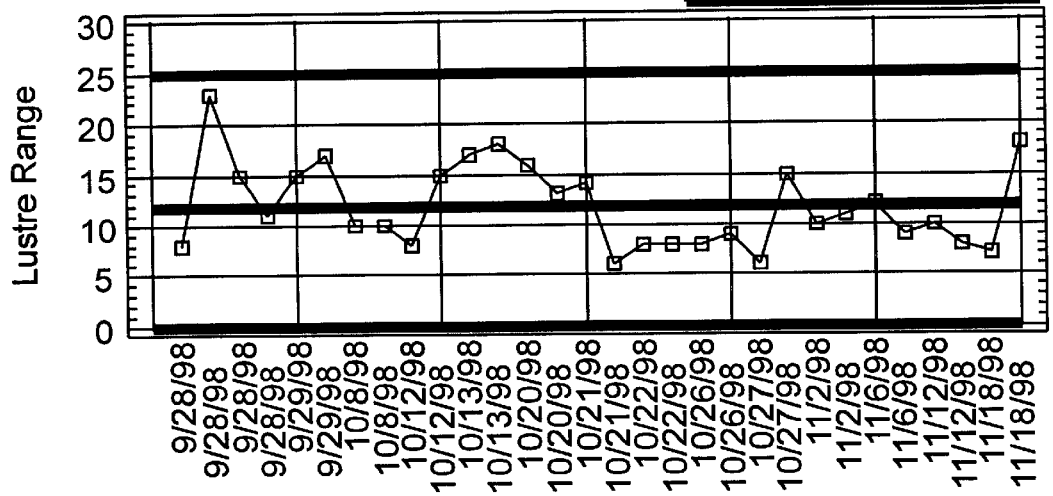
FIG. 10 is a graph depicting coke lustre range chart for Monitor 980029.
Figure 11:
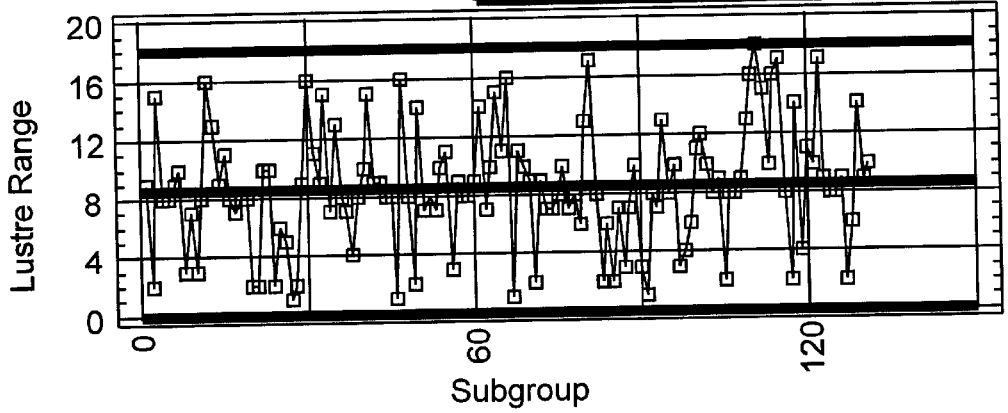
FIG. 11 is a graph depicting lustre range chart for 131 Cokes.
Figure 12:
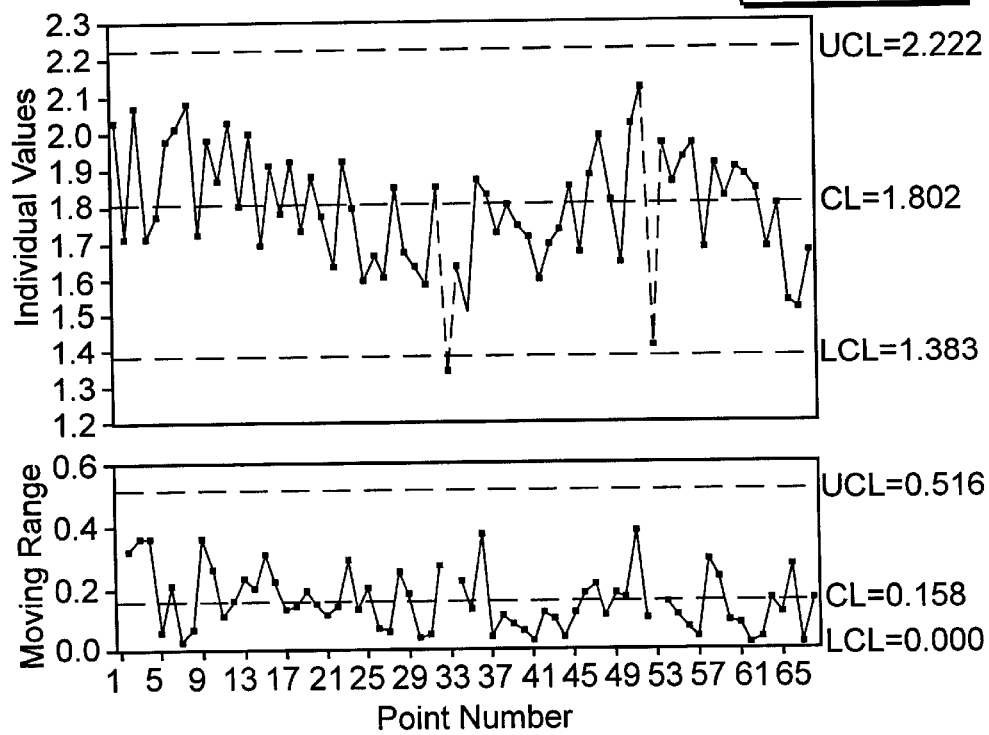
FIG. 12 is a graph depicting Plant A Flour CTE for Monitor 950169.
Figure 13:
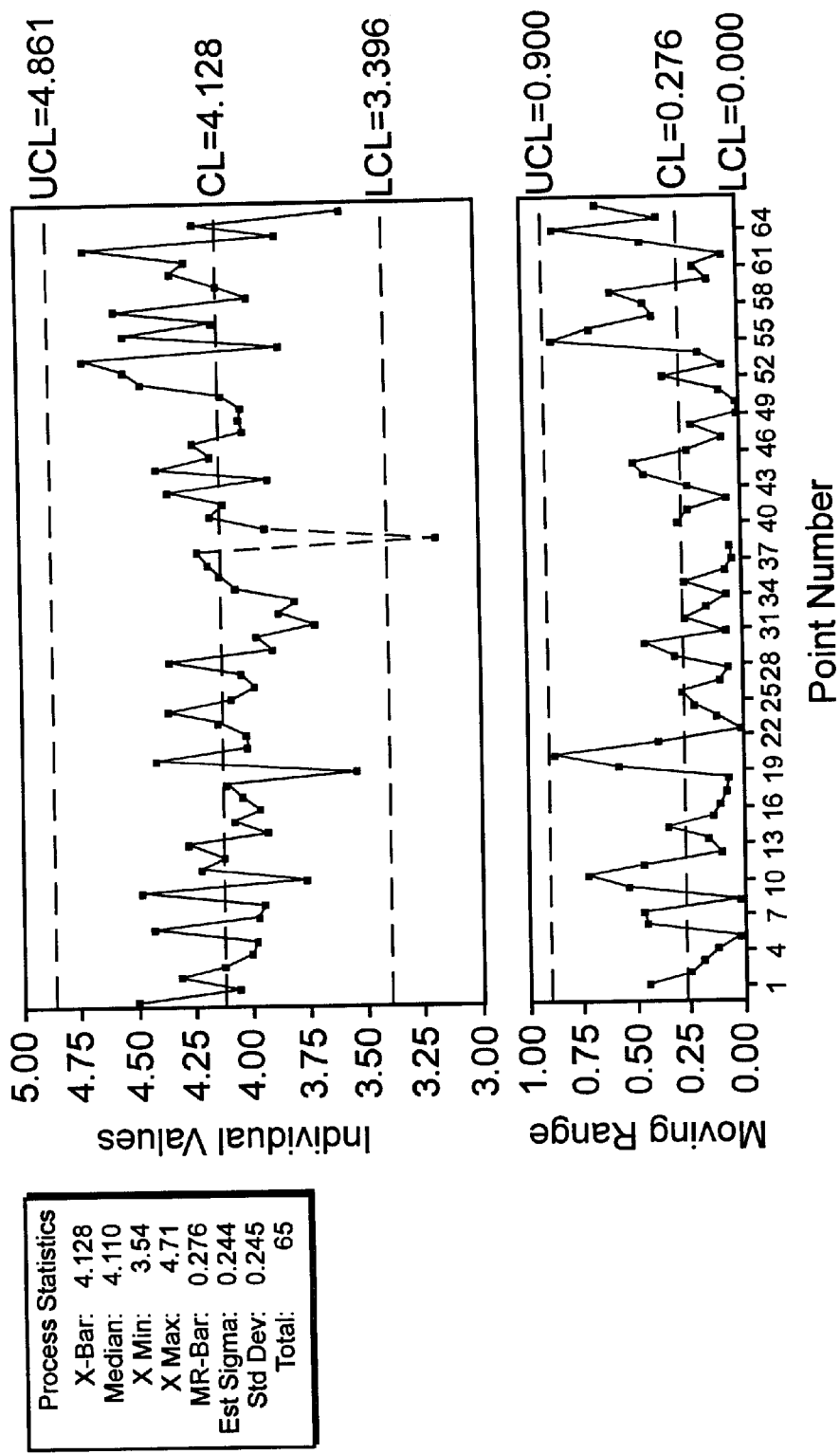
FIG. 13 is a graph depicting Plant A Coarse Grain CTE for Monitor 950169.
Figure 14:
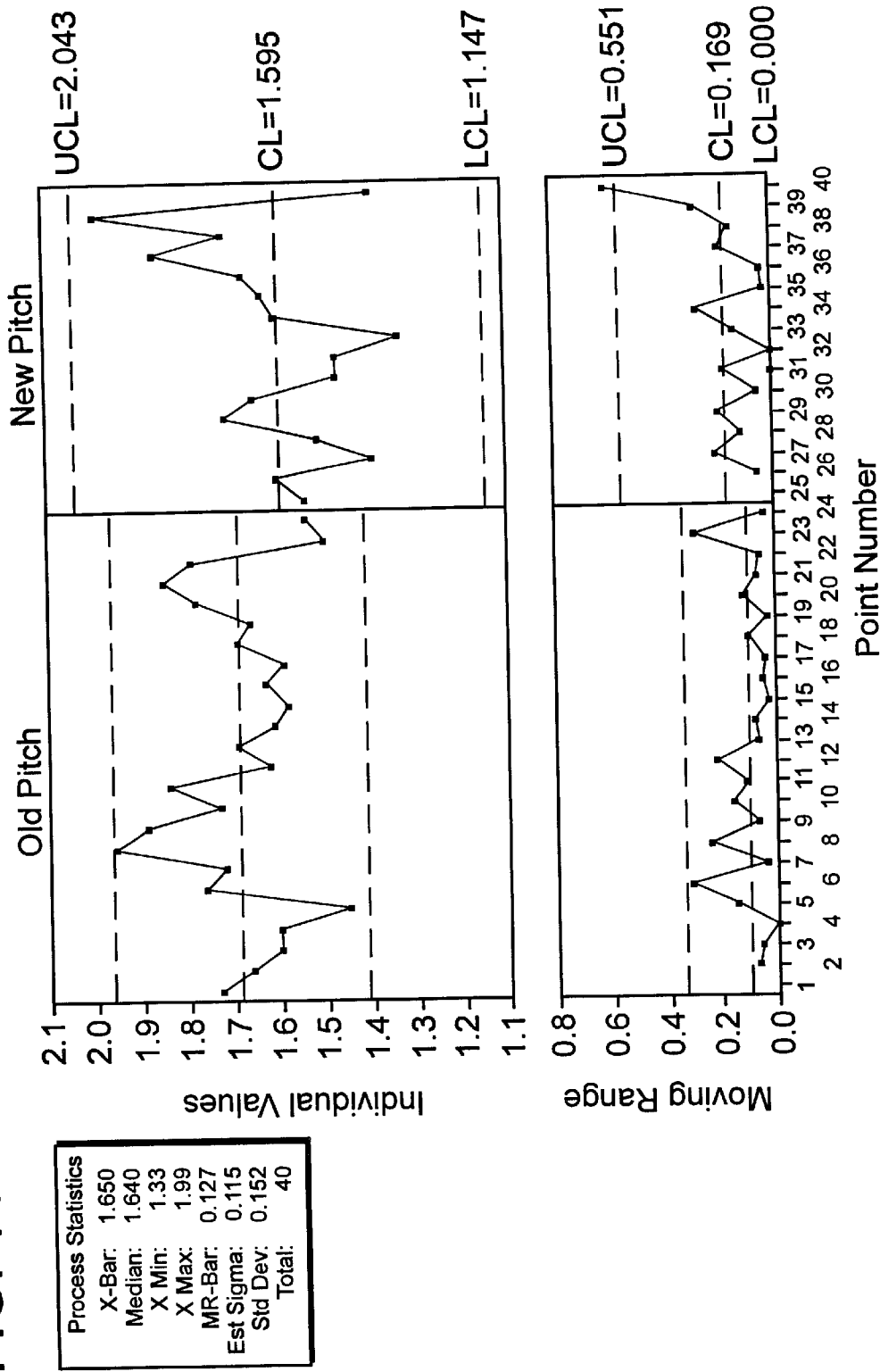
FIG. 14 is a graph depicting Plant A Flour CTE for Monitor 950169.
Figure 15:
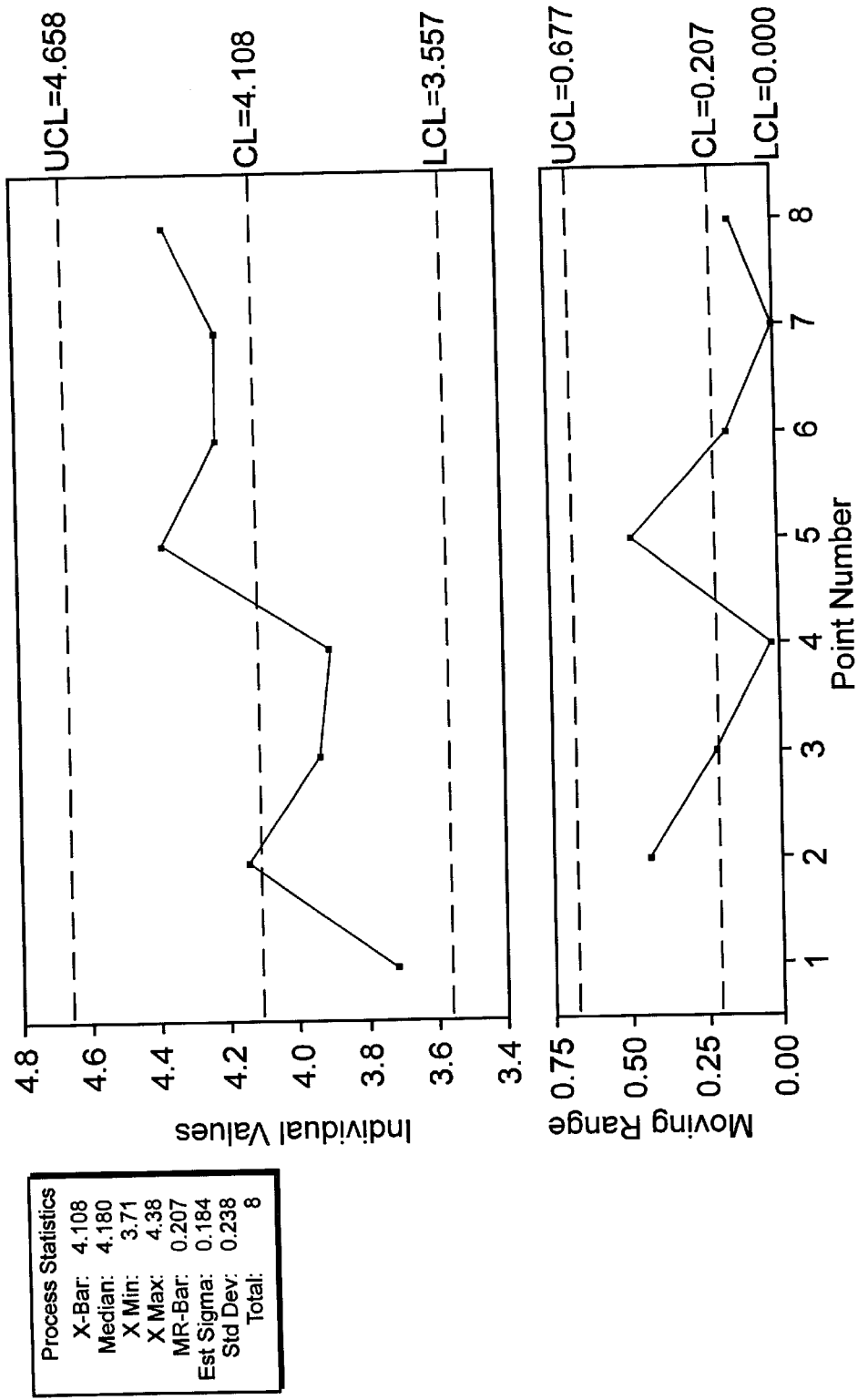
FIG. 15 is a graph depicting Plant B Coarse Grain CTE for Monitor 950169.
Figure 16:
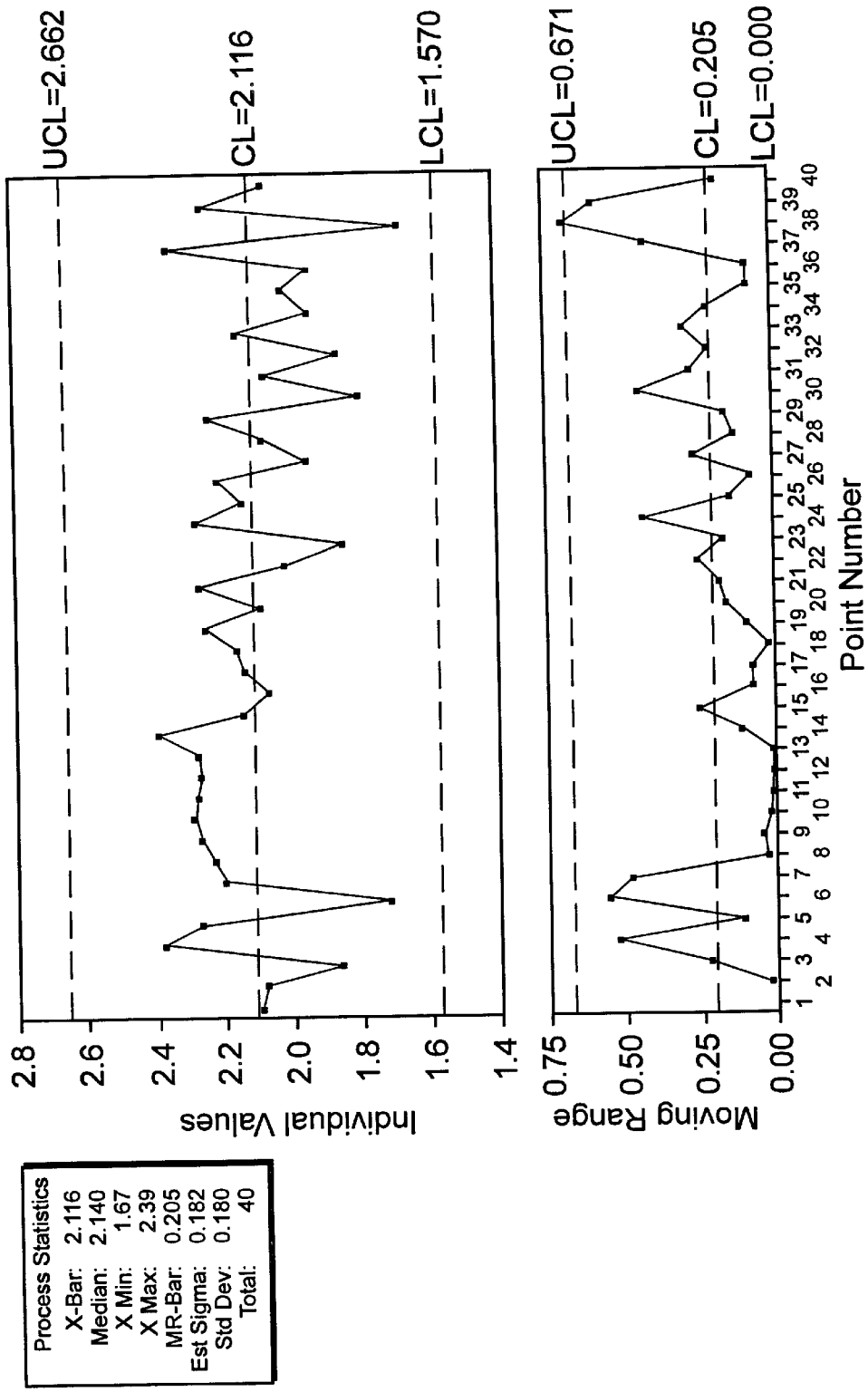
FIG. 16 is a graph depicting Plant C Flour CTE for Monitor 950169.
Figure 17:
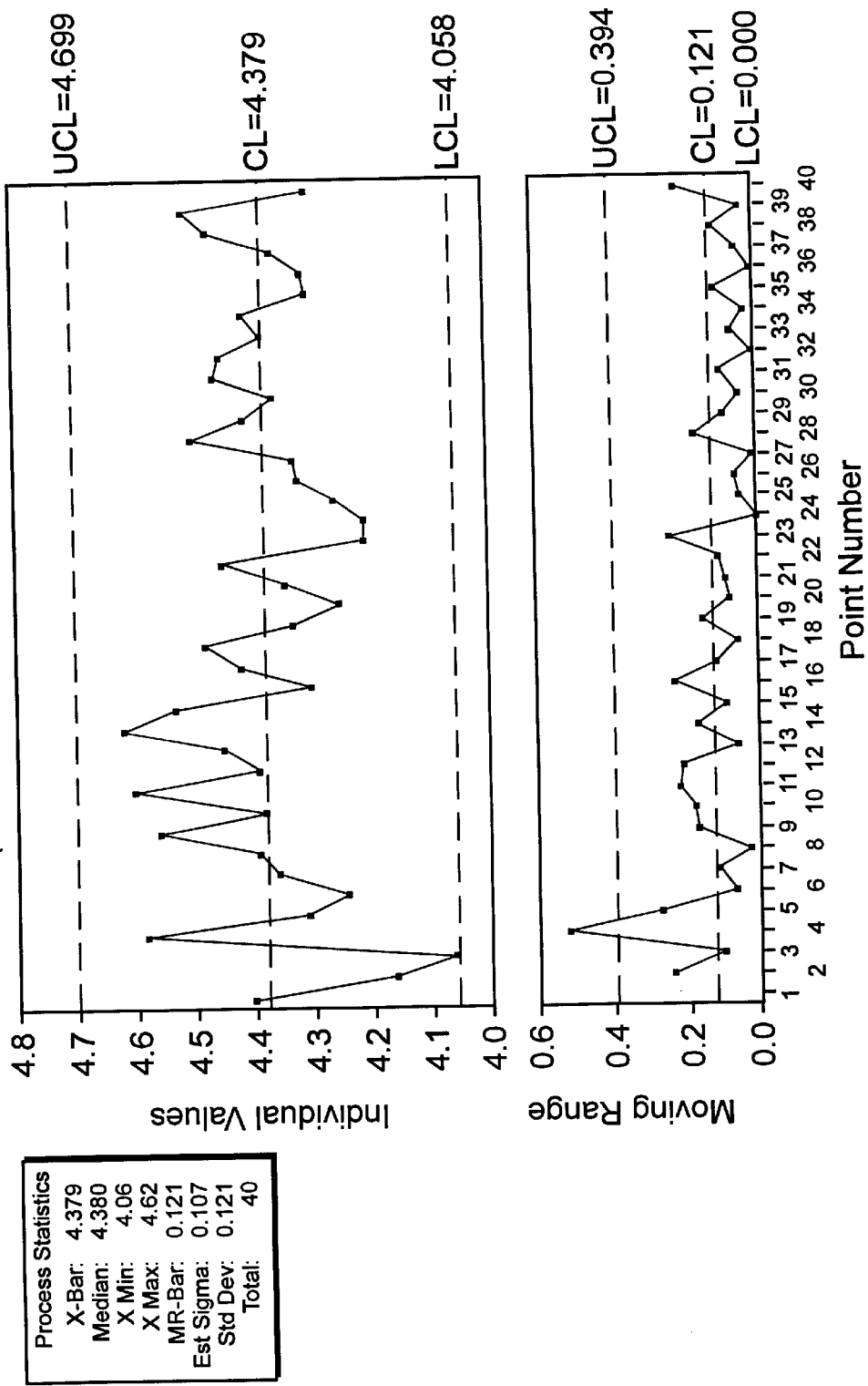
FIG. 17 is a graph depicting Plant C Coarse Grain CTE for Monitor 950169.

Notes:
1. For CTEs data refer to Table C1 and FIGS. 12–14
2. For Lustre data refer to FIGS. 9–10

TABLE 2

CTE Prediction Capability of Lustre Test

| Coke Grade | Actual FCTE | N | Predicted FCTE | Actual CGCTE | N | Predicted CGCTE | Lustre | N |
| --- | --- | --- | --- | --- | --- | --- | --- | --- |
| Plant B | | | | | | | | |
| N | 4.9 | 8 | 4.8 | | | | 97 | 8 |
| M | 3.1 | 11 | 3.0 | | | | 123 | 11 |
| J | 2.0 | 5 | 1.9 | 3.9 | 3 | 3.5 | 144 | 5 |
| F | 1.2 | 22 | 1.3 | 2.5 | 22 | 2.5 | 160 | 22 |
| Plant A | | | | | | | | |
| K | 2.0 | 13 | 1.9 | 4.7 | 13 | 4.5 | 130 | 13 |
| E | 1.2 | 44 | 1.1 | 3.0 | 44 | 2.9 | 164 | 44 |
| G | 1.3 | 5 | 1.6 | 3.5 | 5 | 3.8 | 145 | 5 |
| A | 0.2 | 15 | 0.4 | 1.4 | 15 | 1.5 | 196 | 15 |
| Other Cokes | | | | | | | | |
| L | 2.1 | 2 | 1.6 | 3.6 | 2 | 3.2 | 146 | 2 |
| D | 1.0 | 1 | 1.2 | 2.3 | 1 | 2.6 | 168 | 1 |
| B | 0.9 | 1 | 0.6 | 1.8 | 1 | 1.8 | 217 | 1 |
| H | 1.3 | 1 | 1.5 | 3.5 | 1 | 3.0 | 152 | 1 |
| C | 0.9 | 2 | 1.3 | 3.0 | 2 | 2.7 | 162 | 2 |
| I | 1.7 | 1 | 1.9 | 3.0 | 1 | 3.7 | 135 | 1 |

Notes:
1. Plant B CTE predictions: (based on plant generated CTEs)
FCTE = −4.139 + 871.23/Lustre (see FIG. 4)
CGCTE = 1/(1.347 − 152.12/Lustre); $R^2$ = 29.2%
2. Plant A CTE predictions: (based on plant generated CTEs)
FCTE = 5.051 − 0.024*Lustre (see FIG. 3a)
CGCTE = 10.46 − 0.046*Lustre (see FIG. 3b)
3. Other cokes CTE predictions: (based on Plant C CTEs)
FCTE = −1.570 + 464.82/Lustre; $R^2$ = 50.2%
CGCTE = 1/(−0.199 + 0.0035*Lustre); $R^2$ = 81.8%

What is claimed is:

1. A method for testing a petroleum product produced during refining to classify said product, said method comprising the steps of:
   a) obtaining and preparing a representative sample of said product;
   b) placing said sample beneath an illuminating device in a manner that promotes formation of a substantially smooth upper surface;
   c) illuminating said upper surface with visible light to produce a visible light pattern from light reflected from said upper surface due to the illumination thereof;
   d) forming a digital image of said upper surface from said visible light pattern obtained by acquiring a plurality of images from said visible light pattern;
   e) processing said digital image by extracting and filtering said digital image to produce a representative lustre measurement of said sample wherein said steps b) through e) are iterated a plurality of times and including the additional step of totalling said representative lustre measurement of said sample produced during each of said iterations and then averaging said total to obtain an average lustre measurement of said sample; and
   f) comparing said average lustre measurement to established parameters to assign a coefficient of thermal expansion (CTE) value to said sample to determine the CTE of said product, given historical correlation between CTE and lustre measurements.

2. The method as recited in claim 1 wherein said step of illuminating said sample includes slightly magnifying said sample.

3. The method as recited in claim 1 wherein said digital image processing step uses apparatus having pattern recognition digital processing functions capable of producing and defining said image as having a low or high coefficient of thermal expansion (CTE).

4. The method as recited in claim 3 further including the step of repeating all previous steps for successive samples and designating each sample as to low or high CTE.

5. The method as recited in claim 1 further including the step of varying known operating parameters during petroleum refining to alter said lustre measurement of said sample in order to obtain a product with a desirable CTE.

6. A method for testing a petroleum product in particle form produced during refining to classify said product, said method comprising the steps of:
   a) obtaining and preparing a representative sample from said product;
   b) placing said sample beneath an illuminating device in a manner that promotes the formation of a substantially smooth upper surface;
   c) illuminating said upper surface with visible light from a desired direction to produce a visible light pattern from light reflected from said upper surface due to the illumination thereof;
   d) forming a digital image of said materials from said visible light pattern, said image being an average image obtained by acquiring a plurality of consecutive images from said visible light pattern;
   e) processing said digital image to produce a representative digital measurement of said sample and subsequently extracting and filtering said digital measurement to produce a representative lustre measurement of said sample using apparatus having pattern recognition digital processing functions capable of producing and defining said video image as having a low or high CTE;
   f) repeating steps b) through e) a plurality of times while totalling said representative lustre measurement of said sample produced and subsequently averaging said total to obtain an average lustre measurement of said sample; and
   g) comparing said average lustre measurement to established parameters to assign a CTE value to said sample to determine the CTE of said product.

7. The method as recited in claim 6 wherein said step of illuminating said sample includes slightly magnifying said sample.

8. The method as recited in claim 6 further including the step of varying said known operating parameters during petroleum refining to alter said lustre measurement of said sample in order to obtain a product with a desirable CTE.

9. A process for obtaining a coke having a desirable coefficient of thermal expansion (CTE) by varying known operating parameters during petroleum refining that produces various products including coke, said process comprising the steps of:
   a) obtaining and preparing at least one representative sample from said coke produced during said refining;
   b) analyzing said representative sample to determine a lustre value for said sample;
   c) correlating said lustre value to CTE to obtain a sample CTE; and,
   d) comparing said sample CTE with said desirable CTE and altering said operating parameters.

10. A process as set forth in claim 9 including the additional steps of:
   repeating steps a) and b) for additional samples of additional coke produced; and
   blending said cokes having different lustres to achieve said desirable CTE.

11. The process as recited in claim 9 wherein said step of analyzing said representative sample includes the steps of:
   a) placing said sample beneath an illuminating device in a manner that promotes the formation of a substantially smooth upper surface;
   b) illuminating said upper surface with visible light from a desired direction to produce a slightly magnified visible light pattern from light reflected or emitted from said upper surface due to the illumination thereof;
   c) forming a digital image of said materials from said visible light pattern, said image being an average image obtained by acquiring a plurality of consecutive images from said visible light pattern;
   d) processing said digital image to produce a representative digital measurement of said sample and subsequently extracting and filtering said digital measurement to produce a representative lustre measurement of said sample; and,
   e) repeating steps a) through d) a plurality of times while totalling said representative lustre measurement of said sample produced and subsequently averaging said total to obtain an average lustre measurement of said sample.

12. The process as recited in claim 11 wherein said processing step uses apparatus having pattern recognition digital processing functions capable of producing and defining said video image as having a low or high CTE.

13. The process as recited in claim 12 further including the step of repeating all previous steps for successive samples and designating each sample as to low or high CTE.

14. The process as recited in claim 13 wherein said production parameters that may be varied include feedstocks, temperature and pressure.

15. The process as recited in claim 14 wherein said samples are obtained during said refining.

16. A method for testing a petroleum product in particle form to classify the product, said method comprising the steps of:
   a) preparing a level, loosely packed bed of said particles;
   b) placing said bed of particles beneath an illuminating device;
   c) illuminating a top surface area of said bed of particles to produce a visible reflection of light from said top surface area; and
   d) determining an intensity measurement of said reflected light by extracting measurements above a certain threshold and discarding measurements below said threshold.

17. A method as set forth in claim 16 including the additional step of repeating steps a) through d) a plurality of times to obtain an average lustre measurement.

18. A method as set forth in claim 16 including the additional step of comparing said intensity measurement against established parameters.

19. A method as set forth in claim 16 wherein said illuminating does not polarize said light.

20. A method as set forth in claim 16 wherein said visible reflection of light is quantified by measuring gray levels present and wherein said step of determining an intensity measurement is accomplished by selecting gray levels over a certain threshold.

* * * * *